United States Patent [19]

Lafon

[11] Patent Number: 4,663,328
[45] Date of Patent: May 5, 1987

[54] 3-PHENYL-TETRAHYDROPYRIDINE DERIVATIVES, AND THEIR USE AS SEDATIVE AGENTS

[75] Inventor: Louis Lafon, Paris, France

[73] Assignee: Laboratoire L. Lafon, France

[21] Appl. No.: 823,596

[22] Filed: Jan. 29, 1986

[30] Foreign Application Priority Data

Feb. 1, 1985 [FR] France .................. 85 01410

[51] Int. Cl.$^4$ .................. C07D 211/70; A61K 31/44
[52] U.S. Cl. ...................... 514/277; 546/348
[58] Field of Search .................. 546/348; 514/277

[56] References Cited

U.S. PATENT DOCUMENTS

| 2,748,140 | 5/1956 | Schmidle et al. | 546/348 |
| 3,125,488 | 3/1964 | Biel | 546/348 |
| 3,458,521 | 7/1966 | Jack et al. | 546/348 |
| 4,263,438 | 4/1981 | Altheus et al. | 546/348 |

FOREIGN PATENT DOCUMENTS

| 1455825 | 9/1966 | France | 546/348 |
| 2496099 | 12/1980 | France | 546/348 |

OTHER PUBLICATIONS

Stevens et al. Chem. Abstracts: 193038p, vol. 83 (1975).
Gressner et al. Chem. Abstracts: 68730j, vol. 104 (1986).
Hacksell, et al., J. Med. Chem., vol. 24, No. 12, Dec. 1981, pp. 1475–1482.
Stevens et al., J. of the Chemical Society, Chem. Comm. No. 16, p. 682 8/20/75.

Primary Examiner—John M. Ford
Assistant Examiner—J. Richter
Attorney, Agent, or Firm—McDougall, Hersh & Scott

[57] ABSTRACT

The present invention relates, by way of new industrial products, to the N-alkyl-3-phenyl-1,2,5,6- and 1,4,5,6-tetrahydropyridines of the formulae

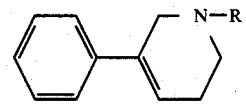 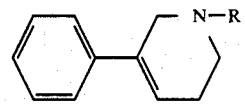

(I)   (I bis)

wherein R is a $C_2$–$C_4$ alkyl group, and their addition salts.

These new products are useful as pharmaceuticals, especially as sedative agents.

7 Claims, No Drawings

4,663,328

3-PHENYL-TETRAHYDROPYRIDINE DERIVATIVES, AND THEIR USE AS SEDATIVE AGENTS

FIELD OF THE INVENTION

The present invention relates to 3-phenyltetrahydropyridine derivatives as new industrial products. It also relates to the method of preparation and the use in therapy of these new compounds.

The new derivatives according to the invention belong to the family of 1,2,5,6- and 1,4,5,6-tetrahydropyridines of the formulae I and I bis presented hereinafter.

PRIOR ART

N-methyl-3-phenyl-1,2,5,6-tetrahydropyridine is known as a laboratory curiosity from the article of R. V. STEVENS et al. Journal of the Chemical Society, Chemical Communications, N. 16, page 682 (1975), this compound (referenced hereinafter as compound A) being obtained by cyclic rearrangement of a phenylcyclobutylimine according to the following mechanism:

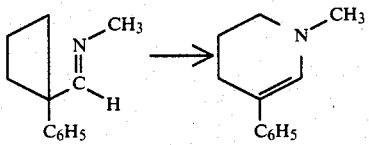

but its eventual pharmaceutical properties being not disclosed in said article.

A method of preparation of N-alkyl-3-phenylpiperidines by reduction of 3-phenylpyridines into 3-phenylpiperidines then N-alkylation is also known from the article of U. HACKSELL et al., J. Med. Chem., 24, 1475–1482 (1981) whereby said reduction reaction does not lead to 3-phenyl-1,2,5,6-tetrahydropyridines.

Are known from FR-A No. 2,496,099 N-alkyl-3-(3-hydroxyphenyl)-1,2,5,6-tetrahydropyridine derivatives which are presented as substances exhibiting agonist or antagonist dopaminergic properties.

It is known from the disclosure of U.S. Pat. No. 4,263,438 that N-alkyl- and N-benzyl-3-phenyl-1,2,5,6-tetrahydropyridine derivatives, in which the phenyl group in 3-position of the tetrahydropyridine nucleus comprises two substituents, have been presented as intermediate compounds in the preparation of 3-phenylpiperidine derivatives which are useful as analgesic agents.

It is also known from FR-A No. 1,455,825 that N-alkyl-4-(halogenophenyl)-1,2,3,6-tetrahydropyridine derivatives have been presented as vermifuge substances.

OBJECT OF THE INVENTION

According to the invention are provided new N-alkyl-3-phenyl-1,2,5,6- and/or 1,4,5,6-tetrahydropyridine derivatives, which are structurally different from the products of the above cited prior art, exhibit interesting properties on the central nervous system (CNS), act in the organism as sedative agents and have the advantage of not exhibiting harmful teratogenic effects.

DETAILED DISCLOSURE OF THE INVENTION

The new 3-phenyl-tetrahydropyridine derivatives according to the invention are characterized in that they are selected from the group comprising
 (i) the N-alkyl-3-phenyl-1,2,5,6- and 1,4,5,6-tetrahydropyridines of the formulae

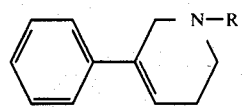 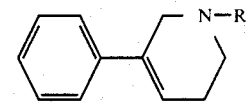

(I)  (I bis)

wherein R represents a $C_2$–$C_4$ alkyl group, and their mixtures; and,
 (ii) addition salts thereof.

Amongst the $C_2$–$C_4$ alkyl groups of R which are suitable according to the invention, can be cited in particular $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$ and $C(CH_3)_3$. The most interesting compounds from a therapeutical point of view are those wherein R is $CH_2CH_3$ or $CH(CH_3)_2$.

The expression "addition salts" is understood here as meaning firstly the acid addition salts obtained by reacting a free base of the formula I or I bis with inorganic or organic acids, and secondly the ammonium salts. Hydrochloric, hydrobromic, acetic, propionic, oxalic, fumaric, maleic, succinic, benzoic, cinnamic, mandelic, citric, malic, tartaric, aspartic, glutamic, methanesulfonic and p-toluenesulfonic acids may be mentioned in particular among the acids which can be used to salify the bases of the formula I or I bis. $CH_3I$ and $CH_3Cl$ may be mentioned in particular among the compounds making it possible to obtain ammonium salts. In general terms, the acid addition salts are preferred to the ammonium salts.

Taking into account the method of preparation given hereinafter, each 3-phenyl-tetrahydropyridine derivative according to the invention is a compound of the formula I, a compound of the formula I bis or a mixture of both 1,2,5,6-tetrahydro and 1,4,5,6-tetrahydro isomers. In the light of present knowledge it is strongly believed that the "1,2,5,6-tetrahydro" structure is the predominant one in the formula of the compounds according to the invention. This is the reason why, for convenient purpose, the expression "3-phenyl-1,2,5,6-tetrahydropyridine" designates hereinafter not only the compounds of the 1,2,5,6-tetrahydro structure, but also those of the 1,4,5,6-tetrahydro structure and mixtures of both structures.

A number of compounds according to the invention have been collated in Table I below without in any way implying a limitation.

TABLE I

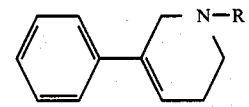

| Product | Code Number | R |
|---|---|---|
| Ex 1 (a) | CRL 41 244 | $CH(CH_3)_2$ |
| Ex 2 (a) | — | $C(CH_3)_3$ |
| Ex 3 (b) | CRL 41 244 A | $CH(CH_3)_2$ |
| Ex 4 (c) | CRL 41 244 B | $CH(CH_3)_2$ |

TABLE I-continued

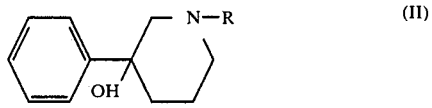

| Product | Code Number | R |
| --- | --- | --- |
| Ex 5 (b) | — | C(CH$_3$)$_3$ |
| Ex 6 (a) | CRL 41 124 | CH$_2$CH$_3$ |

Notes:
(a): hydrochloride
(b): fumarate
(c): methanesulfonate

The compounds according to the invention can be prepared in accordance with a method known per se, by application of classical reaction mechanisms. The method recommended here consists in subjecting a N-alkyl-3-hydroxy-3-phenylpiperidine of the formula $$\text{(II)}$$

(wherein R is defined as indicated above) to a dehydratation reaction. Advantageously said reaction is carried out in acidic medium, and more advantageously in a CH$_3$COOH—CH$_3$COX mixture (wherein X is a halogen atom, in particular F, Cl or Br, and preferably Cl).

The best mode for carrying out said method consists in reacting a reaction medium comprising a N-alkyl-3-hydroxy-3-phenylpiperidine of the formula II and a CH$_3$COOH—CH$_3$COCl (1:1) v/v mixture, for at least 1 h at the reflux temperature of said reaction medium.

The compounds according to the invention exhibits valuable therapeutical properties. In particular they act on the CNS, especially as sedative agents.

According to the invention, a therapeutical composition is recommended which contains, in association with a physiologically acceptable excipient, at least one compound of the formula I (or I bis) or one of its addition salts as the active principle.

Of course, in a composition of this type, the active principle, which is selected from the group consisting of the compounds of the formula I or I bis and their nontoxic salts, is present in a pharmaceutically effective quantity.

The preferred compounds according to the invention are the N-ethyl-, N-isopropyl- and N-t-butyl-3-phenyl-1,2,5,6-tetrahydropyridines and their addition salts. The most interesting compounds from a pharmaceutical point of view are (i) the N-isopropyl-3-phenyl-1,2,5,6-tetrahydropyridine and its non-toxic addition salts, and (ii) the N-ethyl-3-phenyl-1,2,5,6-tetrahydropyridine and its non-toxic addition salts.

Further advantages and characteristics of the invention will be understood more clearly on reading the following description of preparative examples and the results of pharmacological tests; these data as a whole do not imply a limitation but are given by way of illustration.

PREPARATION I

Preparation of N-isopropyl-3-phenyl-1,2,5,6-tetrahydropyridine hydrochloride.

(EXAMPLE 1; CODE NO: CRL 41 244).

Alternative nomenclature: 1-isopropyl-3-phenyl-1,2,5,6-tetrahydropyridine hydrochloride.

A reaction mixture consisting of 0.02 mol of N-isopropyl-3-hydroxy-3-phenylpiperidine, 50 ml of acetic acid and 50 ml of acetyl chloride was heated at reflux temperature for 2 hours. After evaporation to dryness, the evaporation residue was taken up with acetone, and the precipitate thus formed was filtered. Recrystallization from acetone-ethanol (1:1) v/v gave CRL 41 244 with a yield of 49%. Melting point (inst.)=160° C.

PREPARATION II

Obtention of N-isopropyl-3-phenyl-1,2,5,6-tetrahydropyridine hydrochloride (CRL 41 244) by total synthesis.

The total synthesis is schematically represented on diagram A below.

(a) N-Benzyl-3-hydroxy-3-phenyl-piperidine hydrochloride 50 g (0.222 mol) of N-benzyl-3-piperidinone were dissolved in water, and NaOH was added up to pH 11. Extraction was carried out with diethyl ether, the ether phase was then washed with water, dried over MgSO$_4$ and filtered. Into the filtrate thus obtained cooled by means of an ice bath and kept under a nitrogen atmoshere, was poured a solution (3 mol, 90 cm$^3$) of phenylmagnesium bromide in ether. When the addition of C$_6$H$_5$MgBr was completed, the reaction medium was left to reach room temperature (15°–20° C.) then poured into 1 kg of ice. The ether phase was recovered by decantation, washed with water and dried over MgSO$_4$. After filtration (in order to discard MgSO$_4$), the expected hydrochloride was precipitated by means of HCl-containing ethanol. By recrystallization from acetone-ethanol (1:1) v/v, 8.8 g (yield: 13%) of N-benzyl-3-hydroxy-3-phenylpiperidine hydrochloride were obtained.

Analysis % Cl$^-$ measured: 12.08%; % Cl$^-$ theoretical: 11.70%.

(b) 3-Hydroxy-3-phenylpiperidine hydrochloride.

8.8 g (0.029 mol) of N-benzyl-3-hydroxy-3-phenylpiperidine hydrochloride were dissolved in 400 ml of methanol, Pd/C (1.60 g) in suspension in anhydrous ethanol was added, then the resulting medium was contacted with H$_2$. After absorption of 700 ml of H$_2$, the reaction medium was filtered and the filtrate was evaporated to dryness. The evaporation residue was taken up with ether and the formed precipitate was dried to give 4.5 g [yield of steps (a)+(b): 9.5%] of 3-hydroxy-3-phenylpiperidine hydrochloride. Melting point (inst.)=244° C. (with decomposition).

Analysis % Cl$^-$ measured: 16.86%; % Cl$^-$ theoretical: 16.63%.

(c) N-Isopropyl-3-hydroxy-3-phenylpiperidine hydrochloride.

A reaction medium comprising 28.3 g (0.132 mol) of 3-hydroxy-3-phenylpiperidine, 24.77 g (0.146 mol) of isopropyl iodide, 46.4 g (0.438 mol) of CO$_3$Na$_2$ and 300 ml of H$_2$O was brought to reflux temperature for 4 hours. After cooling, extraction with ether, washing with water the ether phase drying said ether phase over MgSO$_4$ and filtering of MgSO$_4$, the expected hydrochloride was precipitated from the filtrate thus obtained, by addition of HCl-containing ethanol. By recrystallization from acetone-ethanol (1:1) v/v, 23 g (yield: 68%) of N-isopropyl-3-hydroxy-3-phenylpiperidine hydrochloride were obtained. Melting point (inst.) = 194° C. (with decomposition).

(d) CRL 41 244

A mixture of 10 g (0.039 mol) of N-isopropyl-3-hydroxy-3-phenylpiperidine hydrochloride, 60 ml of $CH_3COOH$ and 60 ml of $CH_3COCl$ was heated to reflux temperature for 2 h. After evaporation to dryness, taking up the evaporation residue with acetone, the formed precipitate was collected. By recrystallization from acetone-ethanol (1:1) v/v/, 5 g (yield: 54%) of CRL 41 244 were obtained. Melting point (inst.) = 160° C.

PREPARATION III

Preparation of N-t-butyl-3-phenyl-1,2,5,6-tetrahydropyridine hydrochloride

(EXAMPLE 2)

By following the procedure indicated in step (d) of Preparation II and replacing the N-isopropyl-3-hydroxy-3-phenylpiperidine hydrochloride with the N-tert.-butyl-3-hydroxy-3-phenylpiperidine hydrochloride, the N-tert.-butyl-3-phenyl-1,2,5,6-tetrahydropyridine hydrochloride was obtained.

PREPARATION IV

Preparation of N-ethyl-3-phenyl-1,2,5,6-tetrahydropyridine hydrochloride

(EXAMPLE 6; CODE NO: CRL 41 124).

8.4 g (0.0348 mol) of N-ethyl-3-hydroxy-3-phenylpiperidine hydrochloride were dissolved in 50 ml of $CH_3COOH$. 50 ml of $CH_3COCl$ were added and the resulting mixture was heated to reflux temperature for 2 hours (with a $CaCl_2$ gard). After evaporation to dryness and taking up the evaporation residue with ethyl acetate, the formed precipitate was filtered. By recrystallization from acetone-ethanol (1:1) v/v 4 g (yield: 51%) of CRL 41 124 were obtained. Melting point (inst.) = 180° C.

The results of the tests which were undertaken with the products of Example 1 (CRL 41 244) and Example 6 (CRL 41 124), which are the preferred compounds according to the invention, have been summarized below. In these tests, unless stated otherwise, the products were administered intraperitoneally in solution in distilled water at pH 6 (CRL 41 244) and at pH 5 (CRL 41 124), in a volume of 20 ml/kg to male mice and in a volume of 5 ml/kg to male rats.

A—ASSAYS REGARDING CRL 41 244
(EXAMPLE I)

I. Toxicity

The LD-50 on i.p. administration to male mice is of the order of about 90 mg/kg and the LD-0 (maximum non-lethal dose) is of the order of 30 mg/kg.

II. Overall Behaviour and Reactivities

Groups of 6 animals are observed before and then 15 minutes, 30 minutes, 1 hour, 2 hours, 3 hours and 24 hours after the administration of CRL 41 244. In mice, the observations made at the following doses are:

0.125 mg/kg:
 hypothermia (maximum −0.9° C.) for 0.5 h;
0.5 mg/kg:
 sedation (for 2/6 animals) 0.25 h after administration,
 diminution of the respiration (2/6) and in the reaction of fear (3/6) 0.25 h after administration,
 hypothermia (maximum: −1.9° C.) for more than 1 hour;
2 mg/kg:
 sedation for about 1 h,
 diminution of the respiration (at 0.15 h) and in the reaction of fear (for 1 h),
 hypothermia (maximum: −1.7° C.) for more than 1 h; and,
8 mg/kg:
 sedation for about 1 h,
 diminution in the reaction of fear (for 1 h) and in the reactivity to touch (for 1 h),
 moderate mydriasis for 0.5 h, and
 dyspnoea for 1 h.

III. Action on Rectal Temperature

The rectal temperature of mice (6 animals per dose) is measured every 30 minutes during 3 h, after administration of CRL 41 244 per i.p. route. From the dose of 0.032 mg/kg, CRL 41 244 induces a hypothermia which reaches its maximum intensity between 0.5 and 1 h and which has a duration of 2 h; the maximum effect is observed at the dose of 0.5 mg/kg.

IV. Interaction with Apomorphine

1. In mice

Groups of 6 mice receive CRL 41 244 by intraperitoneal administration half an hour before the subcutaneous injection of 1 or 16 mg/kg of apomorphine. It is found that, at the dose of 8 mg/kg, CRL 41 244 antagonizes the hypothermia induced by apomorphine without modifying the righting (verticalization) behaviour and stereotypies induced by apomorphine, and that at lower doses (0.125 mg/kg, 0.5 mg/kg and 2 mg/kg) CRL 41 244 causes a potentiation of the apomorphine-induced hypothermia.

2. In rats

CRL 41 244 is administered intraperitoneally to groups of 6 rats half an hour before the subcutaneous injection of 0.5 mg/kg of apomorphine. It is found that, CRL 41 244 does not modify the stereotypies induced by apomorphine in rats.

V. Interaction with Amphetamine

Amphetamine (2 mg/kg) is injected intraperitoneally into groups of 6 rats half an hour after the intraperitoneal administration of CRL 41 244. It is found that, at the dose of 4 mg/kg, CRL 41 244 moderately diminishes the stereotypies induced by amphetamine.

VI. Interaction with Reserpine

Four hours after the intraperitoneal injection of 2.5 mg/kg of reserpine, groups of 12 mice receive CRL 41 244 by intraperitoneal administration for the purpose of studying the action of the product on temperature and ptosis. It is observed that CRL 41 244 does not modify the hypothermia and the ptosis induced by reserpine.

VII. Interaction with Oxotremorine

CRL 41 244 is administered intraperitoneally to groups of 6 mice half an hour before the intraperitoneal injection of 0.5 mg/kg of oxotremorine.

1. Action on the temperature

CRL 41 244, which administered alone, exerts a hypothermic effect, does not modify the temperature drop induced by oxotremorine.

2. Action on the trembling

The intensity of the tremblings due to the oxotremorine is weakly diminished by CRL 244 at doses of 2 and 8 mg/kg.

3. Action on the peripheral cholinergic symptoms

CRL 41 244 does not modify distinctly the peripheral cholinergic stimulation signs induced by oxotremorine.

VIII. Action on the Four Plate Test, Traction and Electric Shock.

The test is performed on groups of 10 mice half an hour after the intraperitoneal administration of CRL 41 244. It is observed that CRL 41 244 causes a moderate decrease in the number of punished passes, that is does not cause major motor deficiency and that, it does not modify the convulsant and lethal effects of electric shock.

IX. Action on the Spontaneous Motility

Half an hour after they have received CRL 41 244 by intraperitoneal administration, the mice (12 per dose, 24 control animals) are placed in an actimeter, where their motility is recorded for 30 minutes. It is found that, as from the dose of 0.032 mg/kg, CRL 41 244 causes hypomotility. The maximum intensity of the effect is quickly obtained (0.25 mg/kg) and the effect is maintained at a level of 50% of diminishing for higher doses (comprised between 0.25 mg/kg and 8 mg/kg).

X. Action on the Intergroup Aggressiveness

After they have stayed for 3 weeks in the two halves of a cage divided by an opaque partition, groups of 3 mice receive CRL 41 244 by intraperitoneal administration. Half an hour later, the two groups from the same cage are brought together by removal of the partition, and the number of fights which occur in 10 minutes is noted. It is noted that, as from the dose of 0.25 mg/kg, CRL 41 244 highly reduces the number of fights; this effect seems to desappear at the strongest tested dose (2 mg/kg).

XI. Action Towards Some Forms of Behaviour Perturbed by Various Agents.

1. Motility reduced by habituation to the enclosure

After they have stayed in the actimeters for 18 hours, the mice (6 per dose, 12 control animals) receive CRL 41 244 by intraperitoneal administration. They are immdiately returned to their respective enclosures and, half an hour later, their motility is recorded for 30 minutes. It is observed that CRL 41 244 does not cause a resumption in the motor activity of mice accustomed to their enclosure.

2. Motility reduced by hypoxic aggression

Half an hour after they have received CRL 41 244 by intraperitoneal administration, the mice (10 per dose, 20 control animals) are subjected to acute hypobaric anoxia [pressure reduction of 600 mm Hg (i.e. about $8 \times 10^4$ pascals) in 90 seconds; release of vacuum in 45 seconds] and are then placed in an actimeter, where their motility is recorded for 10 minutes. It is observed that, as from the dose of 0.125 mg/kg, CRL 41 244 causes a decrease in the motor recovery in mice whose motility has been depressed following a brief period in a reduced-pressure enclosure.

3. Asphyxiant anoxia

Groups of 10 mice receive CRL 41 244 by intraperitoneal administration half an hour before the intraperitoneal administration of 32 mg/kg of gallamine triiodoethylate (reference curarizing agent).

It is observed that, as from the dose of 0.125 mg/kg, CRL 41 244 significantly increases the time taken for convulsions and death to occur following asphyxiant anoxia caused by a curarizing agent.

XII. Interaction with Barbital

Half an hour after the intraperitoneal administration of CRL 41 244, groups of 10 mice receive an intra peritoneal injection of barbital (220 mg/kg). It is found that CRL 41 244 does not mofify the duration of the sleep induced by barbital.

XIII. Action on the "Behavioral Despair"

Half an hour after they have received CRL 41 244 by intraperitoneal administration, groups of 6 male mice are placed in a beaker filled with water to a height of 6 cm. The total period of immobility between the 2nd and 6th minutes following immersion is noted. It is observed that, at a dose of 16 mg/kg, CRL 41 244 does not modify the period of immobility or so-called period of "despair".

XIV. Conclusions.

The results of the above neuropsychopharmacological assays show that CRL 41 244 is a sedative agent.

Clincal assays, which were carried out, allow to determine that the daily dose to administrate per os to adult human beings is comprised between 1 mg and 6 mg of CRL 41 244. In particular, good results were obtained during those clinical assays after oral administration of 2 to 3 tablets or gelatine capsules (containing each from 1 to 2 mg of CRL 41 244) per day.

B—ASSAYS REGARDING CRL 41 124
(EXAMPLE 6)

Here are the results obtained while using the protocols disclosed above for CRL 41 244.

I. Toxicity

On male mice per i.p. route CRL 41 124 exhibits a LD-0 of the order of about 50 mg/kg and a LD-30 (lethal dose for 30% of the animals) of the order of about 60 mg/kg.

II. Overall Behaviour and Reactivities

In mice, the observations made at the following doses are:

0.25 mg/kg:
no distinct modification of behaviour and reactivities with respect to control animals;

1 mg/kg:
sedation 1 h after administration, and hypothermia (maximum: $-1°$ C., 30 minutes after administration) for 1 h;

4 mg/kg:
sedation for about 1 h,
polypnoea 0.5 h after administration,
mydriasis 0.5 h after administration, and 16 mg/kg:
sedation for 3 h,
polypnoea for 1 h,
piloerection,
decrease in the reactivity to touch and the muscular tonus,
moderate mydriasis 0.5 h after administration, and
hypothermia ($-1.3°$ C. 0.5 h after administration) with a duration of 2 h.

III. Interaction with Apomorphine

1. In mice

It is observed that CRL 41 124, at doses of 1 mg/kg, 4 mg/kg and 16 mg/kg, antagonizes the hypothermia induced by apomorphine without modifying the righting behaviour and stereotypies.

2. In rats

CRL 41 124 does not modify the stereotypies induced by apomorphine.

IV. Interaction with Amphetamine

CRL 41 124 does not modify the stereotype movements induced by amphetamine.

V. Interaction with Reserpine

It is observed that CRL 41 124 does not modify the hypothermia induced by reserpine, but that it causes a moderate reduction of the reserpine-induced ptosis (at the dose of 16 mg/kg).

VI. Interaction with Oxotremorine

It is found that CRL 41 124, which used alone exerts a hypothermia, antagonized at the doses of 4 and 16 mg/kg, the hypothermia induced by oxotremorine.

CRL 41 124 does not modify (i) the trembling and (ii) seems not to modify the peripheral cholinergic stimulation signs caused by oxotremorine.

VII. Action on the Four Plate Test, Traction and Electric Shock

CRL 41 124 does not induce an increase in the number of punished passes. It does not cause major motor deficiency, does not modify the convulsivant effects but increases at a strong dose (16 mg/kg) the lethal effects of electric shock.

VIII. Action on the Spontaneous Motility

As from the dose of 0.01 mg/kg, CRL 41 124 causes a decrease in the spontaneous motility of mice.

IX. Action on the Intergroup Aggressiveness

It is observed that CRL 41 124 (at doses of 0.06 and 0.25 mg/kg) causes a decrease in the number of fights.

X. Action Towards Some Forms of Behaviour Perturbed by Various Agents

1. Motility reduced by habituation to the enclosure

CRL 41 124 does not cause a resumption in the motor activity of mice accustomed to their enclosure.

2. Motility reduced by hypoxic aggression

It is observed that, as from the dose of 0.25 mg/kg, CRL 41 124 causes a decrease in the motor recovery in mice whose motility has been depressed following a brief period in a reduced-pressure enclosure.

3. Asphyxiant anoxia

CRL 41 124 does not modify the time taken for convulsions and death to occur following asphyxiant anoxia caused by a curarizing agent.

XI. Interaction with Barbital

CRL 41 124 does not tend to modify the duration of the sleep induced by barbital.

XII. Action on the "Behavorial Despair"

CRL 41 124 does not modify the period of immobility of mice placed in forced immersion.

XIII. Conclusions

The above assays point out that CRL 41 124 acts as a sedative agent and exhibits CNS-antidepressant effects.

C. COMPARATIVE ASSAYS

A teratogenic study was undertaken on Burgundy female rabbits, weighting each about 2900 grams before gestation. The rabbits of the Burgundy species have a fawn-coloured fur and the female generally have a litter of 2 to 10 young.

On day 1 of gestation (i.e. the day on which male rabbit is placed in the females' cage), Burgundy female rabbits were divided into batches of 10 animals per dose and product to be tested and a batch of 15 animals as control. The female rabbits were administered with daily doses of 0 (control animals) 1 and 5 mg/kg of products to be tested by gastrogavage from day 5 to day 18 of gestation. The a cesarean operation was carried out on day 28 of gestation in order to enumerate (i) the number of female rabbits presenting in their litter at least one foetus malformation, and (ii) the total number of foetus presenting one or several malformations.

The results obtained are given in Table II below. They show that the compounds according to the invention do not exhibit the harmful teratogenic effect of the comparison product (A) disclosed by STEVENS et al. supra.

TABLE II

Teratogenic study.

| Compound | Code Number | Dose (mg/kg) | TTF (a) | FFM (b) Number | % | TNF (c) | FPM (d) Number | % |
|---|---|---|---|---|---|---|---|---|
| Control batch | — | 0 | 15 | 0 | 0 | 72 | 0 | 0 |
| Ex 1 | CRL 41 244 | 1 | 10 | 0 | 0 | 52 | 0 | 0 |
| Ex 1 | CRL 41 244 | 5 | 10 | 0 | 0 | 48 | 0 | 0 |
| Ex 2 | — | 1 | 10 | 0 | 0 | 47 | 0 | 0 |
| Ex 2 | — | 5 | 10 | 0 | 0 | 54 | 0 | 0 |
| Ex 6 | CRL 41 124 | 1 | 10 | 0 | 0 | 47 | 0 | 0 |
| Ex 6 | CRL 41 124 | 5 | 10 | 0 | 0 | 55 | 0 | 0 |
| A (e) | — | 1 | 10 | 1 | 10 | 49 | 5 | 10.2 |
| A (e) | — | 5 | 10 | 2 | 20 | 52 | 9 | 17.3 |

Notes:
(a) TTF = total number of control or treated female rabbits during gestation
(b) FFM = female rabbits having in their litter at least one foetus presenting malformation
(c) TNF = total number of foetus
(d) FPM = foetus presenting malformation.
(e) comparison product, namely N—methyl-3-phenyl-1,2,5,6-tetrahydropyridine hydrochloride, disclosed by STEVENS et al. Journal of the Chemical Society, Chemical Communications No. 16, page 682 (1975)

DIAGRAMME A

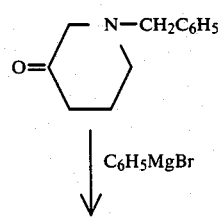

TABLE II-continued

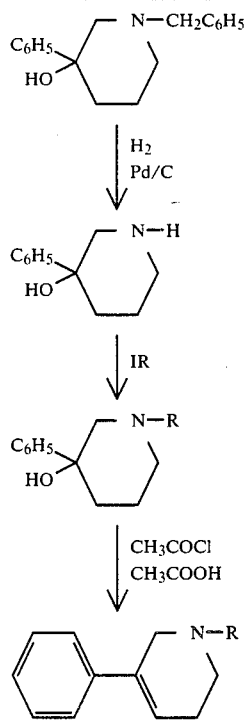

What is claimed is:

1. A 3-phenyl-tetrahydropyridine derivative selected from the group consisting
   (i) the N-alkyl-3-phenyl-1,2,5,6- and 1,4,5,6-tetrahydropyridines of the formulae

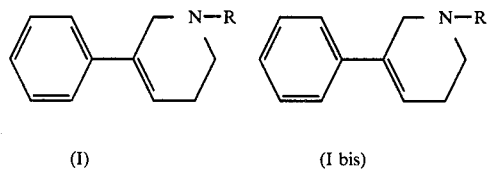

(I)  (I bis)

wherein R represents a $C_2$-$C_4$ alkyl group, and, their mixtures; and,
   (ii) addition salts thereof.

2. A derivative according to claim 1, in which R represents $CH_2CH_3$, $CH(CH_3)_2$ or $C(CH_3)_3$.

3. N-Isopropyl-3-phenyl-1,2,5,6-tetrahydropyridine and addition salts thereof.

4. N-Ethyl-3-phenyl-1,2,5,6-tetrahydropyridine and addition salts thereof.

5. A therapeutical sedative composition comprising, in association with a physiologically acceptable excipient, a pharmaceutically sedative effective amount of a compound of the formula I or I bis according to claim 1 or one of its non-toxic addition salts.

6. A therapeutical sedative composition according to claim 5, which comprises a pharmaceutically sedative effective amount of a compound selected from the group comprising N-isopropyl-3-phenyl-1,2,5,6-tetrahydropyridine, N-ethyl-3-phenyl-1,2,5,6-tetrahydropyridine and non-toxic addition salts thereof.

7. A method of treatment of excitation which comprises administering to a patient in need of such a treatment a sedative amount of a sedative compound selected from the group comprising N-alkyl-3-phenyl-1,2,5,6-tetrahydropyridines of the formula I according to claim 1, N-alkyl-3-phenyl-1,4,5,6-tetrahydropyridines of the formula I bis according to claim 1, and non-toxic addition salts thereof.

* * * * *